(12) United States Patent
Tanaka et al.

(10) Patent No.: US 6,710,210 B2
(45) Date of Patent: Mar. 23, 2004

(54) N-SUBSTITUTED-AMINOMETHYL CYCLOPROPYL KETONE DERIVATIVES OR SALTS THEREOF AND PRODUCTION PROCESS THEREFOR

(75) Inventors: Hiroki Tanaka, Arai (JP); Li Rui Pan, Arai (JP); Kiyoshi Ikura, Arai (JP)

(73) Assignee: Daicel Chemical Industries, Ltd., Osaka (JP)

( * ) Notice: Subject to any disclaimer, the term of this patent is extended or adjusted under 35 U.S.C. 154(b) by 0 days.

(21) Appl. No.: 10/117,233

(22) Filed: Apr. 8, 2002

(65) Prior Publication Data

US 2002/0156323 A1 Oct. 24, 2002

(30) Foreign Application Priority Data

Apr. 23, 2001 (JP) ........................................ 2001-124499

(51) Int. Cl.[7] .............................................. C07C 225/10
(52) U.S. Cl. ...................... 564/344; 564/376; 564/384; 564/386; 564/446; 564/447; 564/448
(58) Field of Search ................................ 564/374, 376, 564/384, 386, 446, 447, 448

(56) References Cited

FOREIGN PATENT DOCUMENTS

| FR | 2168947 A | 9/1973 |
|----|-----------|--------|
| WO | WO 00/09481 | 2/2000 |

OTHER PUBLICATIONS

Database CAPLUS on STN, Acc. No. 2000:133659, WO2000009481 (abstract).*
Beilstein, Database Crossfire, XP002207161, Journal of Organic Chemistry, vol. 40, 1975, pp. 961–963.
Seki et al., *Chem. Pharm. Bull.*, vol. 36, No. 11, 1988, pp. 4435–4440.

* cited by examiner

*Primary Examiner*—Brian Davis
(74) *Attorney, Agent, or Firm*—Birch, Stewart, Kolasch & Birch, LLP

(57) ABSTRACT

Novel N-substituted-aminomethyl cyclopropyl ketone derivatives are represented by following Formula (1):

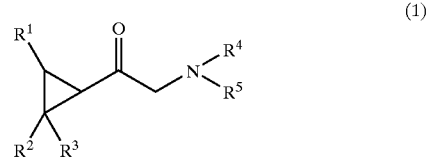

(1)

wherein $R^1$, $R^2$ and $R^3$ are each a hydrogen atom or an aliphatic hydrocarbon group; and $R^4$ and $R^5$ are each a hydrogen atom or an arylmethyl group which may have a substituent, where at least one hydrogen atom or aryl group as a substituent is combined with a carbon atom in the methyl moiety of the arylmethyl group, and at least one of $R^4$ and $R^5$ is an arylmethyl group which may have a substituent. These compounds are useful for the preparation of aminomethyl cyclopropyl ketone derivatives and 2-amino-1-cyclopropylethanol derivatives or salts thereof.

9 Claims, No Drawings

N-SUBSTITUTED-AMINOMETHYL CYCLOPROPYL KETONE DERIVATIVES OR SALTS THEREOF AND PRODUCTION PROCESS THEREFOR

BACKGROUND OF THE INVENTION

1. Field of the Invention

The present invention relates to a novel N-substituted-aminomethyl cyclopropyl ketone derivative or a salt thereof and a production process therefor, as well as to production processes for an aminomethyl cyclopropyl ketone derivative or a salt thereof, for an 2-amino-1-cyclopropylethanol derivative or a salt thereof and for a N-substituted-2-amino-1-cyclopropylethanol derivative or a salt thereof, using the N-substituted-aminomethyl cyclopropyl ketone derivative or a salt thereof as a starting material.

2. Description of the Related Art

Aminomethyl cyclopropyl ketone derivatives, hydrohalide salts thereof, 2-amino-1-cyclopropylethanol derivatives and hydrohalide salts thereof are useful as, for example, pharmaceutical intermediates (e.g., Chem. Pharm. Bull. 36, 11, 4435 (1988)).

Aminomethyl cyclopropyl ketone may be produced by a process, in which an isocyanoacetic ester is allowed to react with an acid chloride to thereby yield an α-C-acylglycine ester, and the α-C-acylglycine ester is then hydrolyzed. However, such an acid chloride used in the process is difficult to handle. The material isocyanoacetic ester is not easily available, since it must be synthetically obtained from a precursor N-formylglycine ester, and the production procedure of the precursor requires highly toxic phosgene. In addition, this process does not provide a sufficient overall yield of aminomethyl cyclopropyl ketone.

Conventionally, 2-amino-1-cyclopropylethanol is produced by a process in which cyclopropanecarboxaldehyde is nitrated and is then reduced. However, this process requires dangerous nitromethane in the nitration step and an expensive reducing agent in the reduction step. In addition, the resulting yield is not satisfactory.

PCT International Publication Number WO 00/09481 describes a synthesis example of a N-benzylaminomethyl cyclopropyl ketone derivative using 2-(3,5-dichlorophenyl)-2-propylamine having two substituents at the benzylic position. However, the resulting N-benzylaminomethyl cyclopropyl ketone derivative obtained by this process cannot yield, through a simple and easy reaction, 2-amino-1-cyclopropylethanol that is practically used as a pharmaceutical intermediate.

SUMMARY OF THE INVENTION

Accordingly, an object of the present invention is to provide a novel N-substituted-aminomethyl cyclopropyl ketone derivative or a salt thereof which are useful for the preparation of aminomethyl cyclopropyl ketone derivatives, 2-amino-1-cyclopropylethanol derivatives, or salts thereof, as well as to provide a production process for the N-substituted-aminomethyl cyclopropyl ketone derivative or a salt thereof.

Another object of the present invention is to provide production processes for an aminomethyl cyclopropyl ketone derivative or a salt thereof and for a N-substituted-2-amino-1-cyclopropylethanol derivative or a salt thereof, which are useful for the preparation of 2-amino-1-cyclopropylethanol derivatives or salts thereof.

A further object of the present invention is to provide a process for efficiently producing an 2-amino-1-cyclopropylethanol derivative or a salt thereof from an easily available material through a simple and easy reaction.

After intensive investigations to achieve the above objects, the present inventors have found that such an aminomethyl cyclopropyl ketone derivative or a salt thereof and an 2-amino-1-cyclopropylethanol derivative or a salt thereof can easily be obtained from a novel N-substituted-aminomethyl cyclopropyl ketone derivative or a salt thereof. The present invention has been accomplished based on these findings.

Specifically, the present invention provides, in one aspect, a N-substituted-aminomethyl cyclopropyl ketone derivative represented by following Formula (1):

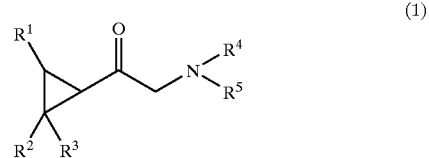

(1)

wherein $R^1$, $R^2$ and $R^3$ are the same or different and are each a hydrogen atom or an aliphatic hydrocarbon group; and $R^4$ and $R^5$ are the same or different and are each a hydrogen atom or an arylmethyl group which may have a substituent, where at least one hydrogen atom or aryl group as a substituent is combined with a carbon atom in the methyl moiety of the arylmethyl group, and at least one of $R^4$ and $R^5$ is an arylmethyl group which may have a substituent, or a salt thereof.

The present invention provides, in another aspect, a process for producing the N-substituted-aminomethyl cyclopropyl ketone derivative represented by Formula (1) or a salt thereof. The process includes the step of aminating a cyclopropyl halomethyl ketone derivative represented by following Formula (2):

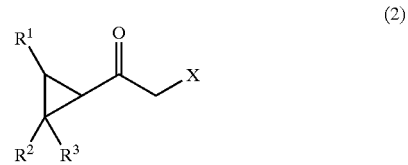

(2)

wherein X is a halogen atom; and $R^1$, $R^2$ and $R^3$ are the same or different and are each a hydrogen atom or an aliphatic hydrocarbon group, by a reaction with a primary or secondary amine represented by following Formula (3):

(3)

wherein $R^4$ and $R^5$ are the same or different and are each a hydrogen atom or an arylmethyl group which may have a substituent, where at least one hydrogen atom or aryl group as a substituent is combined with a carbon atom in the methyl moiety of the arylmethyl group, and at least one of $R^4$ and $R^5$ is an arylmethyl group which may have a substituent.

In a further aspect, the present invention provides a process for producing an aminomethyl cyclopropyl ketone derivative represented by following Formula (4):

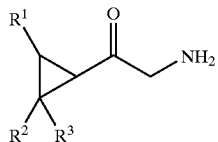

(4)

wherein $R^1$, $R^2$ and $R^3$ have the same meanings as defined above, or a salt thereof. The process includes the step of hydrogenolyzing the N-substituted-aminomethyl cyclopropyl ketone derivative represented by Formula (1) or a salt thereof.

In yet another aspect, the present invention provide a process for producing an 2-amino-1-cyclopropylethanol derivative represented by following Formula (5):

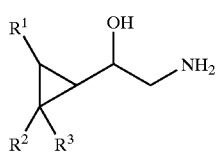

(5)

wherein $R^1$, $R^2$ and $R^3$ have the same meanings as defined above, or a salt thereof. The process includes the steps of hydrogenolyzing the N-substituted-aminomethyl cyclopropyl ketone derivative represented by Formula (1) or a salt thereof to thereby yield the aminomethyl cyclopropyl ketone derivative represented by Formula (4) or a salt thereof, and reducing the resulting compound.

The present invention provides, in another aspect, a process for producing a N-substituted-2-amino-1-cyclopropylethanol derivative represented by following Formula (6):

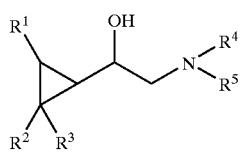

(6)

wherein $R^1$, $R^2$, $R^3$, $R^4$ and $R^5$ have the same meanings as defined above, or a salt thereof. The process includes the step of reducing the N-substituted-aminomethyl cyclopropyl ketone derivative represented by Formula (1) or a salt thereof.

The present invention further provides, in yet another aspect, a process for producing the 2-amino-1-cyclopropylethanol derivative represented by Formula (5) or a salt thereof. The process includes the steps of reducing the N-substituted-aminomethyl cyclopropyl ketone derivative represented by Formula (1) or a salt thereof to thereby yield the N-substituted-2-amino-1-cyclopropylethanol derivative represented by Formula (6) or a salt thereof, and hydrogenolyzing the resulting compound.

In addition and advantageously, the present invention provides a process for producing an aminomethyl cyclopropyl ketone derivative represented by following Formula (8):

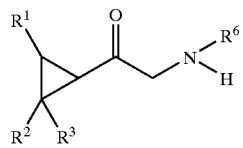

(8)

wherein $R^1$, $R^2$, $R^3$ and $R^6$ have the same meanings as defined above, or a salt thereof. This process includes the step of partially hydrogenolyzing a N-substituted-aminomethyl cyclopropyl ketone derivative represented by following Formula (7):

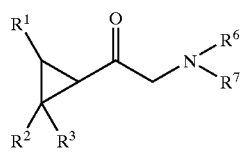

(7)

wherein $R^1$, $R^2$ and $R^3$ have the same meanings as defined above; and $R^6$ and $R^7$ are the same or different and are each an arylmethyl group which may have a substituent, where at least one hydrogen atom or aryl group as a substituent is combined with a carbon atom in the methyl moiety of the arylmethyl group, or a salt thereof.

By these configurations, the present invention can easily yield the novel N-substituted-aminomethyl cyclopropyl ketone derivative or a salt thereof which are useful for the preparation of aminomethyl cyclopropyl ketone derivatives or salts thereof, and 2-amino-1-cyclopropylethanol derivatives or salts thereof.

Further, the present invention can easily produce the aminomethyl cyclopropyl ketone derivative or a salt thereof and the N-substituted-2-amino-1-cyclopropylethanol derivative or a salt thereof which are useful for the preparation of 2-amino-1-cyclopropylethanol derivatives or salts thereof.

In addition, the present invention can efficiently produce the 2-amino-1-cyclopropylethanol derivative or a salt thereof through a simple and easy reaction.

DESCRIPTION OF THE PREFERRED EMBODIMENTS

N-Substituted-aminomethyl Cyclopropyl Ketone Derivatives or Salts Thereof and Production Thereof In the N-substituted-aminomethyl cyclopropyl ketone derivative represented by Formula (1) or a salt thereof, $R^1$, $R^2$ and $R^3$ are the same or different and are each a hydrogen atom or an aliphatic hydrocarbon group.

Such aliphatic hydrocarbon groups include, but are not limited to, methyl, ethyl, propyl, isopropyl, butyl, isobutyl, s-butyl, t-butyl, pentyl, hexyl, decyl, dodecyl, and other alkyl groups each having from about 1 to about 10, and preferably from about 1 to about 4, carbon atoms; vinyl, allyl, 1-butenyl, and other alkenyl groups each having from about 2 to about 10, and preferably from about 2 to about 4, carbon atoms; ethynyl, propynyl, and other alkynyl groups each having from about 2 to about 10, and preferably from about 2 to about 4, carbon atoms.

In Formula (1), $R^4$ and $R^5$ are the same or different and are each a hydrogen atom or an arylmethyl group which may have a substituent, where at least one hydrogen atom or aryl group as a substituent is combined with a carbon atom in the methyl moiety of the arylmethyl group, and at least one of $R^4$ and $R^5$ is an arylmethyl group which may have a substituent. The substituent may be substituted on a carbon atom of whichever of the aryl moiety and the methyl moiety of the arylmethyl group. Such aryl groups include aromatic carbocyclic groups and aromatic heterocyclic groups.

Such aromatic carbocyclic groups include, but are not limited to, phenyl, naphthyl, and other aromatic carbocyclic groups each having from about 6 to about 20, and preferably from about 6 to about 10, carbon atoms. The aromatic heterocyclic groups include, for example, pyridyl group.

Substituents which may be substituted on the aryl moiety of the arylmethyl group include, but are not limited to, halogen atoms (e.g., fluorine, chlorine and bromine atoms), oxo group, hydroxyl group, substituted oxy groups (e.g., methoxy group and other alkoxy groups; aryloxy groups; aralkyloxy groups; and acyloxy groups), carboxyl group, substituted oxycarbonyl groups, substituted or unsubstituted carbamoyl groups, cyano group, nitro group, substituted or unsubstituted amino groups, and alkyl groups (e.g., methyl, ethyl, propyl, isopropyl, and other $C_1$–$C_4$ alkyl groups).

Substituents which may be substituted on a carbon atom of the methyl moiety of the arylmethyl group include, but are not limited to, methyl, ethyl, propyl, isopropyl, butyl, and other alkyl groups (preferably, $C_1$–$C_4$ alkyl groups), the aforementioned aryl groups such as phenyl, naphthyl, pyridyl, and other aromatic carbocyclic groups or aromatic heterocyclic groups which may have a substituent.

In the arylmethyl group, a substituent on the methyl moiety may be combined with the aryl moiety or with a substituent on the aryl moiety to form a ring.

Examples of the arylmethyl group are benzyl, p-chlorobenzyl, p-bromobenzyl, o-nitrobenzyl, p-nitrobenzyl, p-cyanobenzyl, 3,4-dimethoxybenzyl, α-phenylethyl, diphenylmethyl, bis(p-methoxyphenyl) methyl, triphenylmethyl, (p-methoxyphenyl) diphenylmethyl, diphenyl-4-pyridylmethyl, 2-pyridyl-N-oxide, and 5-dibenzosuberyl groups.

Salts of the N-substituted-aminomethyl cyclopropyl ketone derivative include, for example, hydrohalide salts such as hydrochlorides, hydrobromides and hydroiodides; salts of other inorganic acids, such as sulfates, nitrates, carbonates, hydrogencarbonates, phosphates and perchlorates; and salts of organic acids, such as acetates and stearates.

The N-substituted-aminomethyl cyclopropyl ketone derivative represented by Formula (1) or a salt thereof can be obtained by allowing the cyclopropyl halomethyl ketone derivative represented by Formula (2) to react with the primary or secondary amine represented by Formula (3) to thereby replace a halogen atom by a N-substituted amino group.

The cyclopropyl halomethyl ketone derivative represented by Formula (2) used as a substrate is obtained by allowing cyclopropyl methyl ketone to react with a halogen according to a conventional procedure. Such halogens include, for example, chlorine, bromine and iodine.

The reaction between the cyclopropyl halomethyl ketone derivative represented by Formula (2) and the primary or secondary amine represented by Formula (3) is performed in the presence of, or in the absence of, a solvent. Such solvents are not specifically limited, as long as they do not adversely affect the reaction, and include, for example, methanol, ethanol, propanol, t-butyl alcohol, and other alcohols; chloroform, dichloromethane, 1,2-dichloroethane, and other halogenated hydrocarbons; benzene and other aromatic hydrocarbons; hexane, heptane, octane, and other aliphatic hydrocarbons; cyclohexane and other alicyclic hydrocarbons; N,N-dimethylformamide, N,N-dimethylacetamide, and other amides; acetonitrile, propionitrile, benzonitrile, and other nitriles; diethyl ether, t-butyl methyl ether, tetrahydrofuran, and other chain or cyclic ethers; ethyl acetate and other esters; acetic acid and other organic acids; and water. Preferred solvents are methanol, ethanol, propanol, and other alcohols. Each of these solvents can be used alone or in combination. The amount of the solvent is, for example, from about 3 times to about 50 times and preferably from about 5 times to about 10 times that of the charged substrate.

A reaction temperature can appropriately be set depending on the type of the substrate and other factors and is, for example from about 0° C. to about 40° C. and preferably from about 0° C. to about 10° C.

The reaction may be performed at ambient or atmospheric pressure or under a pressure (under a load) in a conventional system such as batch system, semi-batch system or continuous system.

With the proceeding reaction, a hydrogen halide is formed in a reaction system to thereby convert the formed N-substituted-aminomethyl cyclopropyl ketone derivative into a hydrohalide salt thereof. A base may be added to the reaction system to neutralize the hydrohalide salt to thereby yield a free N-substituted-aminomethyl cyclopropyl ketone derivative.

Such bases used in the neutralization include, but are not limited to, sodium carbonate, potassium carbonate, and other alkali metal carbonates; sodium hydrogencarbonate, potassium hydrogencarbonate, and other alkali metal hydrogencarbonates; sodium hydroxide, potassium hydroxide, and other alkali metal hydroxides; magnesium carbonate, calcium carbonate, and other alkaline earth metal carbonates; magnesium hydrogencarbonate, calcium hydrogencarbonate, and other alkaline earth metal hydrogencarbonates; magnesium hydroxide, calcium hydroxide, and other alkaline earth metal hydroxides; and other inorganic bases. Each of these bases can be used alone or in combination.

When the amine represented by Formula (3) is a primary amine, two molecules of the cyclopropyl halomethyl ketone derivative represented by Formula (2) may react with one molecule of the amine represented by Formula (3) under some reaction conditions. The amine represented by Formula (3) is preferably a secondary amine to use the product N-substituted-aminomethyl cyclopropyl ketone derivative represented by Formula (1) or a salt thereof prepared in the reaction as a starting material of the compound represented by Formula (4) or (5) mentioned below.

After the completion of the reaction, reaction products can be separated and purified by such as filtration, concentration, distillation, extraction, crystallization, recrystallization, adsorption, column chromatography, and other separation means or combinations of these separation means.

The free N-substituted-aminomethyl cyclopropyl ketone derivative can be converted into a salt by a reaction with an acid according to a conventional procedure. Such acids include, but are not limited to, hydrofluoric acid, hydrochloric acid, hydrobromic acid, hydroiodic acid, sulfuric acid, nitric acid, and other inorganic acids; formic acid, acetic acid, methanesulfonic acid, and other organic acids. As reaction solvents, the solvents exemplified in the preparation of the N-substituted-aminomethyl cyclopropyl ketone derivative represented by Formula (1) or a salt thereof can be used.

Production of Aminomethyl Cyclopropyl Ketone Derivatives

The aminomethyl cyclopropyl ketone derivative represented by Formula (4) can be obtained by subjecting the N-substituted-aminomethyl cyclopropyl ketone derivative represented by Formula (1) or a salt thereof to hydrogenolysis (hydrocracking).

The hydrogenolysis is generally performed by bringing the N-substituted-aminomethyl cyclopropyl ketone derivative or a salt thereof into contact with hydrogen in a solvent in the presence of a hydrogenolysis catalyst. Such hydrogenolysis catalysts include any conventional hydrogenolysis catalysts, of which a palladium-carbon (activated carbon) catalyst is preferred.

In the palladium-carbon (activated carbon) catalyst, the activated carbon is not specifically limited and includes any activated carbon derived from vegetable materials, mineral materials, polymer materials and other materials by conventional techniques such as gas activation and chemical activation. The activated carbon has a specific surface area of, for example, from about 500 to about 4000 $m^2/g$ and preferably from about 700 to about 4000 $m^2/g$. The amount of palladium on the activated carbon is, for example, from about 1% to about 30% by weight, and preferably from about 3% to about 20% by weight, relative to the weight of the activated carbon.

The amount of the palladium-carbon catalyst is, for example, from about 0.1% to about 20% by weight, and preferably from about 1% to about 10% by weight, relative to the weight of the substrate N-substituted-aminomethyl cyclopropyl ketone derivative or its salt.

Hydrogen for use in the hydrogenolysis is not specifically limited and includes pure hydrogen and hydrogen diluted with an inert gas such as nitrogen, argon or helium gas. A gas phase component can be dissolved in a liquid phase by any technique, as long as the gas phase component is sufficiently dissolved in the liquid phase. For example, the gas phase component may be dissolved by gas-liquid contact alone or by blowing a gas containing hydrogen into the liquid phase. Instead of hydrogen, $HCOONH_4$, $HCOONH(C_2H_5)_3$, $NaH_2PO_2$, $NH_2NH_2$ and other hydrogen sources can be used.

The amount of hydrogen can appropriately be set depending on the type of the substrate and other factors and is generally molar excess to the substrate.

Solvents for use in this reaction are not specifically limited as long as they do not adversely affect the reaction and can solve reaction components. Such solvents include, for example, methanol, ethanol, propanol, isopropanol, and other alcohols. The solvents should preferably be homogeneously miscible with a solution of the hydrogen halide. The amount of the solvent is generally from about 3 times to about 50 times, and preferably from about 5 times to about 10 times that of the charged substrate.

The reaction rate of the hydrogenolysis can be improved by performing the reaction in the presence of a hydrogen halide. Such hydrogen halides include hydrogen chloride, hydrogen bromide and hydrogen iodide. The hydrogen halide is used as intact or as a solution such as an aqueous solution (a hydrohalogenic acid), an alcohol solution or an ether solution. When the hydrohalogenic acid is used, its concentration is from about 5% to about 36% by weight, and preferably from about 30% to about 36% by weight. The amount of the hydrogen halide is from about 1 to about 5 moles, and preferably from about 1.5 to about 2 moles, relative to 1 mole of the free N-substituted-aminomethyl cyclopropyl ketone derivative or is from about 0.5 to about 4 moles, and preferably from about 0.5 to about 1 mole, relative to 1 mole of the hydrohalide salt of the N-substituted-aminomethyl cyclopropyl ketone derivative.

A reaction temperature is not specifically limited and is preferably from about 10° C. to about 30° C.

The reaction may be performed at atmospheric pressure or under a pressure (under a load). When the reaction is performed under a pressure, the pressure is generally from about 0.1 to about 10 MPa, and preferably from about 0.1 to about 1 MPa. The reaction can be performed in a conventional system such as batch system, semi-batch system or continuous system.

The above reaction yields the aminomethyl cyclopropyl ketone derivative represented by Formula (4) or a salt thereof from the N-substituted-aminomethyl cyclopropyl ketone derivative represented by Formula (1) or a salt thereof. By allowing the substrate to react in the presence of a hydrogen halide, a hydrohalide salt, such as hydrochloride, hydrobromide or hydroiodide, of the aminomethyl cyclopropyl ketone derivative can be obtained.

After the completion of the reaction, reaction products can be separated and purified by such as filtration, concentration, distillation, extraction, crystallization, recrystallization, adsorption, column chromatography, and other separation means or combinations of these separation means.

Production of -N-Substituted-2-amino-1-cyclopropylethanol Derivatives or Salts Thereof The N-substituted-2-amino-1-cyclopropylethanol derivative represented by Formula (6) or a salt thereof can be obtained by reducing the N-substituted-aminomethyl cyclopropyl ketone derivative represented by Formula (1) or a salt thereof.

Reducing agents for use in the reduction are not specifically limited as long as they can convert a ketone into an alcohol and include, for example, $Li/NH_3$ and other reducing agents comprising an alkali metal or alkaline earth metal in combination with ammonia or an amine; isobutylaluminium hydride and other metal hydrides; sodium borohydride and other metal-hydrogen complex compounds; boranes; and hydrogen (catalytic reduction using, for example, a rhodium catalyst). The amount of the reducing agent is from about 0.1 to about 10 moles and preferably from about 0.1 to about 1 mole relative to 1 mole of the substrate N-substituted-aminomethyl cyclopropyl ketone derivative or its salt.

The reaction is generally performed in the presence of a solvent. The solvent is not specifically limited as long as it does not adversely affect the reaction and can appropriately be selected depending on the type of the reducing agent and other factors. Such solvents include, for example, those exemplified in the production of the N-substituted-aminomethyl cyclopropyl ketone derivative or a salt thereof.

A reaction temperature can appropriately be set depending on the types of the reducing agent and the substrate and other factors and is, for example, from about 0° C. to about 200° C. and preferably from about 0° C. to about 100° C. The reaction can be performed in a conventional system such as batch system, semi-batch system or continuous system.

After the completion of the reaction, reaction products can be separated and purified by such as filtration, concentration, distillation, extraction, crystallization, recrystallization, adsorption, column chromatography, and other separation means or combinations of these separation means.

Production of 2-Amino-1-cyclopropylethanol Derivatives or Salts Thereof

Using the N-substituted-aminomethyl cyclopropyl ketone derivative represented by Formula (1) or a salt thereof as a starting material, the 2-amino-1-cyclopropylethanol derivative represented by Formula (5) or a salt thereof can be obtained by (i) a process via the production of the aminomethyl cyclopropyl ketone derivative represented by Formula (4) or a salt thereof or by (ii) a process via the production of the N-substituted-2-amino-1-cyclopropylethanol derivative represented by Formula (6) or a salt thereof.

The process (i) via the production of the aminomethyl cyclopropyl ketone derivative represented by Formula (4) or a salt thereof includes the steps of (A) producing the aminomethyl cyclopropyl ketone derivative represented by Formula (4) or a salt thereof from the N-substituted-aminomethyl cyclopropyl ketone derivative represented by Formula (1) or a salt thereof, and (B) reducing the resulting compound.

As the step (A) of the process (i), the production process of the aminomethyl cyclopropyl ketone derivative or a salt thereof can be applied. In the step (B) of the process (i), the aminomethyl cyclopropyl ketone derivative or a salt thereof as a substrate may be reduced in a similar manner to the production process of the N-substituted-2-amino-1-cyclopropylethanol derivative or a salt thereof.

The process (ii) via the production of the N-substituted-2-amino-1-cyclopropylethanol derivative represented by Formula (6) or a salt thereof includes the steps of (A) producing the N-substituted-2-amino-1-cyclopropylethanol derivative represented by Formula (6) or a salt thereof from the N-substituted-aminomethyl cyclopropyl ketone derivative represented by Formula (1) or a salt thereof, and (B) hydrogenolyzing the resulting compound.

As the step (A) of the process (ii), the production process of the N-substituted-2-amino-1-cyclopropylethanol derivative or a salt thereof can be applied. In the step (B) of the process (ii), the N-substituted-2-amino-1-cyclopropylethanol derivative or a salt thereof as a substrate may be subjected to hydrogenolysis in a similar manner to the production process of the aminomethyl cyclopropyl ketone derivative represented by Formula (4) or a salt thereof.

Partial Hydrogenolysis of N,N-Di-substituted-aminomethyl Cyclopropyl Ketone Derivatives or Salts Thereof The N-substituted-aminomethyl cyclopropyl ketone derivative represented by Formula (8) or a salt thereof can be obtained by partial hydrogenolysis of the N,N-di-substituted-aminomethyl cyclopropyl ketone derivative represented by Formula (7) or a salt thereof. The N,N-di-substituted-aminomethyl cyclopropyl ketone derivative represented by Formula (7) or a salt thereof corresponds to a N-substituted-aminomethyl cyclopropyl ketone derivative represented by Formula (1) or a salt thereof where $R^4$ and $R^5$ are arylmethyl groups each of which may have a substituent.

Using the N,N-di-substituted-aminomethyl cyclopropyl ketone derivative represented by Formula (7) or a salt thereof as a substrate, the hydrogenolysis can be performed in a similar manner to the production process of the aminomethyl cyclopropyl ketone derivative represented by Formula (4) or a salt thereof. The substrate can be subjected to partial hydrogenolysis by setting mild reaction conditions.

To hydrogenolyze only one arylmethyl group of the two arylmethyl groups substituted for hydrogen atoms in the amino group, the reaction may be performed, for example, at a low pressure, at a low temperature, for a short reaction time, using a catalyst having relatively low activity, using a carrier carrying a small amount of a catalyst, or using a small amount of a catalyst.

EXAMPLES

The present invention will be illustrated in further details with reference to several examples below, which are not intended to limit the scope of the invention.

In the examples, NMR spectra were determined with tetramethylsilane as an internal standard at 270 MHz ($^1$H-NMR) using JNM-EX270 available from JEOL Ltd. Coupling constants (Hz) are indicated by J.

Preparation Example 1

Production of Bromomethyl Cyclopropyl Ketone

A total of 23.8 g of cyclopropyl methyl ketone was dissolved in 142.8 g of methanol, and 45.2 g of bromine was added dropwise to the solution while maintaining the temperature of the solution at 10° C. to 15° C., followed by stirring at room temperature for 30 minutes. After the completion of the reaction, the reaction mixture was neutralized with 15.0 g of sodium carbonate, was then filtrated and thereby yielded 212 g of a methanol solution containing 34.5 g of bromomethyl cyclopropyl ketone in a yield of 75%. The product bromomethyl cyclopropyl ketone was subjected to a subsequent step as intact without purification.

Spectral Data $^1$H-NMR (CDCl$_3$) ppm: 0.99–1.57 (m, 4H, cyclopropyl), 2.17–2.26 (m, 1H, CH), 4.02 (s, 2H, CH$_2$).

Example 1

Production of N,N-Dibenzyl-aminomethyl Cyclopropyl Ketone Hydrochloride

A total of 212 g of the methanol solution containing 34.5 g of bromomethyl cyclopropyl ketone was cooled to 5° C. or lower, and 41.8 g of dibenzylamine was added dropwise to the solution while maintaining the temperature of the solution at 5° C. or lower, followed by stirring at room temperature for 30 minutes. After the completion of the reaction, the reaction mixture was stirred at room temperature for further 30 minutes. Next, the reaction mixture was neutralized with 16.8 g of sodium carbonate and then with water and was extracted with toluene. An organic layer was fractionated, was concentrated, and the residue was cooled to 10° C. or lower, followed by dropwise addition of 160 g of 5% by weight hydrochloric acid. After the completion of addition, the resulting crystal was filtrated and thereby yielded 63.2 g of N,N-dibenzyl-aminomethyl cyclopropyl ketone hydrochloride as a colorless crystal.

Spectral Data $^1$H-NMR (CDCl$_3$) ppm: 0.90–1.11 (m, 4H, cyclopropyl), 1.51–1.60 (m, 1H, CH), 3.73 (s, 2H, C(=O)CH$_2$NH$_2$), 4.45–4.62 (m, 4H, NH$_2$CH$_2$Ph), 7.40–7.47 (m, 6H, Ph), 7.65–7.74 (m, 4H, Ph), 13.1 (b, 2H, NH$_2$).

Example 2

Production of N-Benzyl-aminomethyl Cyclopropyl Ketone Hydrochloride

A total of 63.2 g of N, N-dibenzyl-aminomethyl cyclopropyl ketone hydrochloride was dissolved in 316 g of methanol, followed by dropwise addition of 11 g of 33% by weight hydrochloric acid. The inner atmosphere of the reaction system was replaced with nitrogen gas three times, 6.3 g of 5% by weight palladium-carbon was then added to the mixture, and the inner atmosphere of the reaction system was replaced with hydrogen gas three times, followed by stirring at room temperature for 2.5 hours. After the completion of the reaction, the resulting reaction mixture was filtrated using a filter aid (available from Kohjin Co., Ltd. under the trade name of "Cerafloc"), the filtrate was concentrated and thereby yielded 38.3 g of N-benzyl-aminomethyl cyclopropyl ketone hydrochloride as a colorless crystal.

Spectral Data $^1$H-NMR (CDCl$_3$) ppm: 0.97–1.07 (m, 2H, cyclopropyl-CH$_2$), 1.10–1.16 (m, 2H, cyclopropyl-CH$_2$), 1.84–1.91 (m, 1H, CH), 4.04 (t, 2H, J=5.40, NH$_2$CH$_2$Ph), 4.33 (t, J=5.13, C(=O)CH$_2$NH$_2$), 7.37–7.43 (m, 3H, Ph), 7.54–7.63 (m, 2H, Ph), 9.74 (b, 2H, NH$_2$)

Other embodiments and variations will be obvious to those skilled in the art, and this invention is not to be limited to the specific matters stated above.

What is claimed is:

1. An N-substituted-aminomethyl cyclopropyl ketone derivative represented by following Formula (1):

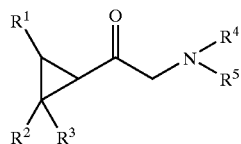

(1)

wherein R$^1$, R$^2$ and R$^3$ are the same or different and are each a hydrogen atom or an aliphatic hydrocarbon group; and R$^4$ is an arylmethyl group which may have a substituent in which the methyl moiety of the arylmethyl group has at least one hydrogen atom or aryl group as a substituent and R$^5$ is the same as or different from R$^4$ and is a hydrogen atom or an arylmethyl group which may have a substituent in which the methyl moiety of the arylmethyl group has at least one hydrogen atom or aryl group as a substituent, or a salt thereof.

2. A process for producing a N-substituted-aminomethyl cyclopropyl ketone derivative or a salt thereof, the process comprising the step of:

aminating a cyclopropyl halomethyl ketone derivative represented by following Formula (2):

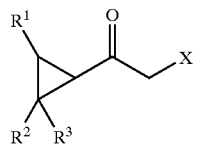

(2)

wherein X is a halogen atom; and R$^1$, R$^2$ and R$^3$ are the same or different and are each a hydrogen atom or an aliphatic hydrocarbon group by a reaction with a primary or secondary amine represented by following Formula (3):

(3)

wherein R$^4$ is an arylmethyl group which may have a substituent in which the methyl moiety of the arylmethyl group has at least one hydrogen atom or aryl group as a substituent and R$^5$ is the same as or different from R$^4$ and is a hydrogen atom or an arylmethyl group which may have a substituent in which the methyl moiety of the arylmethyl group has at least one hydrogen atom or aryl group as a substituent, to thereby yield a N-substituted-aminomethyl cyclopropyl ketone derivative represented by following Formula (1):

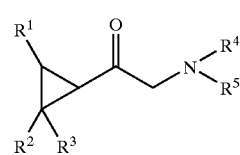

(1)

wherein R$^1$, R$^2$, R$^3$, R$^4$ and R$^5$ have the same meanings as defined above, or a salt thereof.

3. A process for producing an aminomethyl cyclopropyl ketone derivative or a salt thereof, the process comprising the step of:

hydrogenolyzing a N-substituted-aminomethyl cyclopropyl ketone derivative represented by following Formula (1):

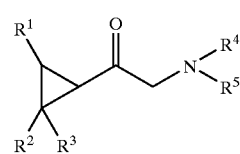

(1)

wherein R$^1$, R$^2$ and R$^3$ are the same or different and are each a hydrogen atom or an aliphatic hydrocarbon group; and R$^4$ is an arylmethyl group which may have a substituent in which the methyl moiety of the arylmethyl group has at least one hydrogen atom or aryl group as a substituent and R$^5$ is the same as or different from R$^4$ and is a hydrogen atom or an arylmethyl group which may have a substituent in which the methyl moiety of the arylmethyl group has at least one hydrogen atom or aryl group as a substituent, or a salt thereof to thereby yield an aminomethyl cyclopropyl ketone derivative represented by following Formula (4):

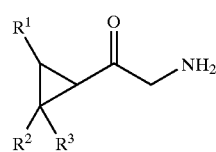

(4)

wherein R$^1$, R$^2$ and R$^3$ have the same meanings as defined above, or a salt thereof.

4. A process for producing an 2-amino-1-cyclopropylethanol derivative or a salt thereof, the process comprising the steps of:

hydrogenolyzing a N-substituted-aminomethyl cyclopropyl ketone derivative represented by following Formula (1):

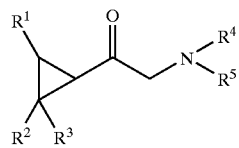

(1)

wherein $R^1$, $R^2$ and $R^3$ are the same or different and are each a hydrogen atom or an aliphatic hydrocarbon group; and $R^4$ is an arylmethyl group which may have a substituent in which the methyl moiety of the arylmethyl group has at least one hydrogen atom or aryl group as a substituent and $R^5$ is the same as or different from $R^4$ and is a hydrogen atom or an arylmethyl group which may have a substituent in which the methyl moiety of the arylmethyl group has at least one hydrogen atom or aryl group as a substituent, or a salt thereof to thereby yield an aminomethyl cyclopropyl ketone derivative represented by following Formula (4):

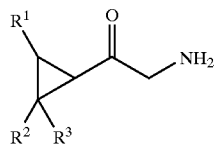

(4)

wherein $R^1$, $R^2$ and $R^3$ have the same meanings as defined above, or a salt thereof; and reducing the resulting compound to thereby yield an 2-amino-1-cyclopropylethanol derivative represented by following Formula (5):

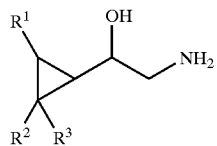

(5)

wherein $R^1$, $R^2$ and $R^3$ have the same meanings as defined above, or a salt thereof.

5. A process for producing a N-substituted-2-amino-1-cyclopropylethanol derivative or a salt thereof, the process comprising the step of:

reducing a N-substituted-aminomethyl cyclopropyl ketone derivative represented by following Formula (1):

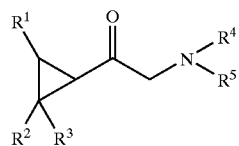

(1)

wherein $R^1$, $R^2$ and $R^3$ are the same or different and are each a hydrogen atom or an aliphatic hydrocarbon group; and $R^4$ is an arylmethyl group which may have a substituent in which the methyl moiety of the arylmethyl group has at least one hydrogen atom or aryl group as a substituent and $R^5$ is the same as or different from $R^4$ and is a hydrogen atom or an arylmethyl group which may have a substituent in which the methyl moiety of the arylmethyl group has at least one hydrogen atom or aryl group as a substituent, or a salt thereof to thereby yield a N-substituted-2-amino-1-cyclopropylethanol derivative represented by following Formula (6):

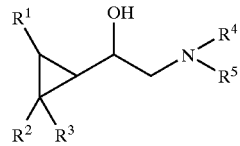

(6)

wherein $R^1$, $R^2$, $R^3$, $R^4$ and $R^5$ have the same meanings as defined above, or a salt thereof.

6. A process for producing an 2-amino-1-cyclopropylethanol derivative or a salt thereof, the process comprising the steps of:

reducing a N-substituted-aminomethyl cyclopropyl ketone derivative represented by following Formula (1):

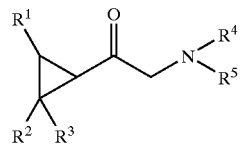

(1)

wherein $R^1$, $R^2$ and $R^3$ are the same or different and are each a hydrogen atom or an aliphatic hydrocarbon group; and $R^4$ is an arylmethyl group which may have a substituent in which the methyl moiety of the arylmethyl group has at least one hydrogen atom or aryl group as a substituent and $R^5$ is the same as or different and is a hydrogen atom or an arylmethyl group which may have a substituent in which the methyl moiety of the arylmethyl group has at least one hydrogen atom or aryl group as a substituent, or a salt thereof to thereby yield a N-substituted-2-amino-1-cyclopropylethanol derivative represented by following Formula (6):

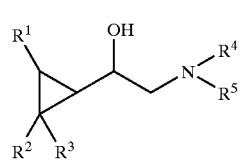

(6)

wherein $R^1$, $R^2$, $R^3$, $R^4$ and $R^5$ have the same meanings as defined above, or a salt thereof; and hydrogenolyzing the resulting compound to thereby yield an 2-amino-1-cyclopropylethanol derivative represented by following Formula (5):

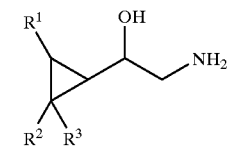

(5)

wherein $R^1$, $R^2$ and $R^3$ have the same meanings as defined above, or a salt thereof.

7. A process for producing an aminomethyl cyclopropyl ketone derivative or a salt thereof, the process comprising the step of:

partially hydrogenolyzing a N-substituted-aminomethyl cyclopropyl ketone derivative represented by following Formula (7):

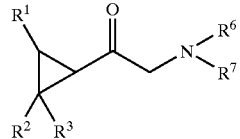

wherein $R^1$, $R^2$ and $R^3$ are the same or different and are each an hydrogen atom or an aliphatic hydrocarbon group; and $R^6$ is an arylmethyl group which may have substituent in which the methyl moiety of the arylmethyl group has at least one hydrogen atom or aryl group as a substituent and $R^7$ is the same as or different from $R^6$ and is an arylmethyl group which may have a substituent in which the methyl moiety of the arylmethyl group has at least one hydrogen atom or aryl group substituent, or a salt thereof to thereby yield an aminomethyl cyclopropyl ketone derivative represented by following Formula (8):

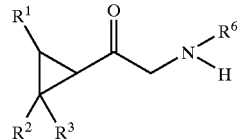

wherein $R^1$, $R^2$, $R^3$ and $R^6$ have the same meanings as defined above, or a salt thereof.

8. The compound of claim 1, identified as N,N-dibenzylaminomethyl cyclopropyl ketone hydrochloride.

9. The compound of claim 1, identified as N-benzylaminomethyl cyclopropyl ketone hydrochloride.

* * * * *